United States Patent
Coury et al.

(10) Patent No.: US 7,008,635 B1
(45) Date of Patent: Mar. 7, 2006

(54) HYDROGELS FOR ORTHOPEDIC REPAIR

(75) Inventors: Arthur J. Coury, Boston, MA (US); Stephen D. Goodrich, Norcross, GA (US); Hildegard M. Kramer, Westport, CT (US); Luis Z. Avila, Arlington, MA (US); John F. Traverse, Somerville, MA (US); Peter K. Jarrett, Sudbury, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/658,390

(22) Filed: Sep. 8, 2000

Related U.S. Application Data

(60) Provisional application No. 60/153,190, filed on Sep. 10, 1999.

(51) Int. Cl.
  *A61F 2/00* (2006.01)
  *A61K 9/00* (2006.01)
  *A61K 9/14* (2006.01)

(52) U.S. Cl. .................. 424/426; 424/423; 424/400; 424/484; 424/487

(58) Field of Classification Search ............... 424/9.1, 424/401, 445, 426, 423, 400, 484, 487; 514/772.3
  See application file for complete search history.

(56) References Cited

U.S. PATENT DOCUMENTS

| | | |
|---|---|---|
| 4,057,535 A | 11/1977 | Lipatova et al. |
| 4,511,478 A | 4/1985 | Nowinski et al. |
| 4,740,534 A | 4/1988 | Matsuda et al. |
| 4,741,872 A | 5/1988 | De Luca et al. |
| 4,804,691 A | 2/1989 | English et al. |
| 4,806,614 A | 2/1989 | Matsuda et al. |
| 4,826,945 A | 5/1989 | Cohn et al. |
| 4,839,345 A | 6/1989 | Doi et al. |
| 4,938,763 A | 7/1990 | Dunn et al. |
| 4,994,542 A | 2/1991 | Matsuda et al. |
| 5,100,992 A | 3/1992 | Cohn et al. |
| 5,160,745 A | 11/1992 | De Luca et al. |
| 5,173,301 A | 12/1992 | Itoh et al. |
| 5,198,507 A | 3/1993 | Kohn et al. |
| 5,219,564 A | 6/1993 | Zalipsky et al. |
| 5,252,714 A | 10/1993 | Harris et al. |
| 5,410,016 A | 4/1995 | Hubbell et al. |

(Continued)

FOREIGN PATENT DOCUMENTS

WO    WO 96/29370 A2    9/1996

(Continued)

OTHER PUBLICATIONS

Corkhill, et al., "The potential of hydrogels as synthetic articular cartilage," *Proc Instn Mech Engs* 204:147-155 (1990).

(Continued)

*Primary Examiner*—Shengjun Wang
(74) *Attorney, Agent, or Firm*—Fish & Richardson P.C.

(57) ABSTRACT

Hydrogels intended for orthopedic applications, including repair and regeneration of cartilage, bone, joint surfaces and related tissues, must possess greater strength and toughness than hydrogels used in soft tissue repair. A hydrogel formulation is provided which has high strength, toughness, a suitable mechanical modulus and low equilibrium hydration. It may also have controlled porosity or degradation time. It can be made to polymerize in situ with high ("good" to "excellent") adherence to target tissue or surfaces. A preferred formulation for forming such gels comprises 40 to 80% by weight of a low-molecular weight polar monomer and 30 to 10% of a hydrophilic macromeric crosslinker.

15 Claims, 1 Drawing Sheet

U.S. PATENT DOCUMENTS

| | | |
|---|---|---|
| 5,514,379 A | 5/1996 | Weissleder et al. |
| 5,573,934 A | 11/1996 | Hubbell et al. |
| 5,583,114 A | 12/1996 | Barrows et al. |
| 5,614,587 A | 3/1997 | Rhee et al. |
| 5,672,662 A | 9/1997 | Harris et al. |
| 5,700,873 A * | 12/1997 | Zajaczkowski et al. ..... 525/283 |
| 5,726,250 A * | 3/1998 | Zajaczkowski ............. 525/296 |
| 5,739,208 A | 4/1998 | Harris |
| 5,744,545 A | 4/1998 | Rhee et al. |
| 5,800,373 A | 9/1998 | Melanson et al. |
| 5,844,016 A | 12/1998 | Sawhney et al. |
| 5,854,382 A | 12/1998 | Loomis |
| 5,874,500 A | 2/1999 | Rhee et al. |
| 5,900,245 A | 5/1999 | Sawhney et al. |

FOREIGN PATENT DOCUMENTS

| | | |
|---|---|---|
| WO | WO 98/00170 A1 | 1/1998 |
| WO | WO 98/12243 A1 | 3/1998 |
| WO | WO 99/03454 A1 | 1/1999 |
| WO | WO 99/07417 A1 | 2/1999 |
| WO | WO 99/14259 | 3/1999 |

OTHER PUBLICATIONS

Lydon, et al., "Cellular interactions with synthetic polymer surfaces in culture," Biomaterials 6(6):396-402 (1985).

* cited by examiner

HYDROGELS FOR ORTHOPEDIC REPAIR

This application claims priority to U.S. Ser. No. 60/153,190, filed Sep. 10, 1999.

FIELD OF THE INVENTION

This invention is generally in the field of treatments of disease, particularly disease of skeletal or orthopedic tissues such as cartilage and bone, using polymeric materials having high adherence to tissue, low degree of swelling, toughness and biocompatibility.

BACKGROUND OF THE INVENTION

Hydrogel materials are useful in coating, sealing and adhesion of soft tissues, for example as described in U.S. Pat. No. 5,410,016 to Hubbell et al., U.S. Pat. No. 5,800,373 to Melanson et al., and U.S. Pat. Nos. 5,844,016, and 5,900,245 to Sawhney et al. Important properties of these hydrogels are their biocompatibility, their ability to adhere strongly to tissue, and good mechanical compliance, which is appropriately matched to that of the tissue. Biocompatibility is achieved by the use of materials that are especially compatible with tissue, such as polyalkylene oxides, and by a high water content, similar to that of the tissue being coated.

However, these gels are less useful in situations in which the gels are subject to high mechanical stress. An example of such a situation is in the repair of bone and other skeletally-related tissues, such as cartilage, the tibial meniscus, tendons and ligaments, spinal disks, and muscle (collectively, "orthopedic tissues"), or in composite implants intended for such uses. Repair of injuries, disease or defects of orthopedic tissues can be difficult because the gel needs to offer protection to the structures under mechanical stress. Tight adherence to the substrate is often beneficial in achieving this purpose. Repair of articular cartilage is especially difficult. A surface must be provided which is resistant to abrasion and provides cushioning during regeneration and maturation of the cartilage, for example, following implants of tissues, cells or aggregates. On the other hand, appropriate stress transmitted to the cells facilitates appropriate alignment and generation of a normal intercellular matrix. Similar considerations apply to bone regeneration, especially at joints.

Traditional hydrogels are not strong enough to withstand the applied stresses, particularly over the length of time required, especially for long periods of time such as those required for regeneration of bone or connective tissue. Such gels also tend to swell extensively in aqueous environments, which can interfere with mechanical properties of the injured joint or other site. Moreover, hydrogels do not tend to adhere strongly to tissue, especially to moist tissue, or when pre-formed before application to tissue. On the other hand, traditional solid implants (which typically are formed of hydrophobic materials) can be too rigid and brittle, thereby impeding or preventing tissue repair or regeneration. They may also lack lubricity, which can compromise performance in joints, as well as pose a risk of abrasion of the opposing surface.

A material that has the appropriate balance of strength and compliance as well as the biocompatibility of a hydrogel, and that has strong adherence to orthopedic tissues, is needed.

It is an object of the present invention to provide biocompatible hydrogels which strongly adhere to orthopedic tissues.

It is another object of the present invention to provide hydrogels with strong mechanical properties.

It is another object of the present invention to provide monomers from which hydrogels with strong mechanical properties can be formed, and methods of use thereof.

SUMMARY OF THE INVENTION

Polymeric materials have been developed which can be effective in treatment of orthopedic tissues, such as cartilage, bone and accessory structures, and implants. In one embodiment, the material includes a mixture of two components which copolymerize to form a hydrogel that contains hydrophilic and hydrophobic regions. The first component is covalently-crosslinkable, hydrophilic, polymeric, of high biocompatibility, and optionally spontaneously hydrolyzing ("biodegradable"). It is preferably sufficiently hydrophilic to be water-soluble at a temperature between about 0 and 70° C. The second component is more hydrophobic (although it is preferably water-soluble under the same conditions), is covalently polymerizable, provides structural strength and limits the water absorption capacity of the formed gel. Upon reaction in situ in the presence of polymerization initiators bound to or adhered to the tissue ("priming systems"), the resulting polymerized hydrogel adheres tightly to the tissues, and has suitable mechanical properties, including toughness, strength and resiliency to facilitate repair or regeneration of the tissue. It also remains as a hydrogel, retaining the advantages of biocompatibility and lubricity. The hydrogel is optionally biodegradable.

In a second embodiment, the material is predominantly a high-molecular weight, covalently-polymerizable macromer, which is soluble or paste-like at high concentration (e.g., 40% or more by weight) in the formulation, and which can be polymerized to form a tough, adherent, biocompatible coating on tissue.

In a third embodiment, monomers of molecular weight less than about 1 kDa, or mixtures of monomers, are the sole or principal precursors of the material. A significant fraction of the weight of the solution, for example 40% or more, is amphiphilic monomers; functionally hydrophobic monomers form less than about 50% of the mixture; macromers comprise from zero to less than about 30% of the weight, and water is from zero to less than about 40% of the weight.

The polymerized materials have a controlled, low degree of swelling on continued exposure to water, combined with a tensile modulus which may be in excess of 1 MPa and also having a significant elongation to break (e.g., 10% or more). This combination of properties makes the materials tough, resilient, and able to withstand cyclic mechanical stress for extended periods. The material can also be made porous, and thereby permissive of cell or tissue ingrowth in the process of tissue repair. Porosity formation may be intrinsic to the materials or may be provided by pore-forming excipients or processes.

Methods of use of such materials in the treatment, repair or regeneration of tissues are described.

DETAILED DESCRIPTION OF THE INVENTION

I. Hydrogel Compositions

A. Required Hydrogel Properties

Figure 1:
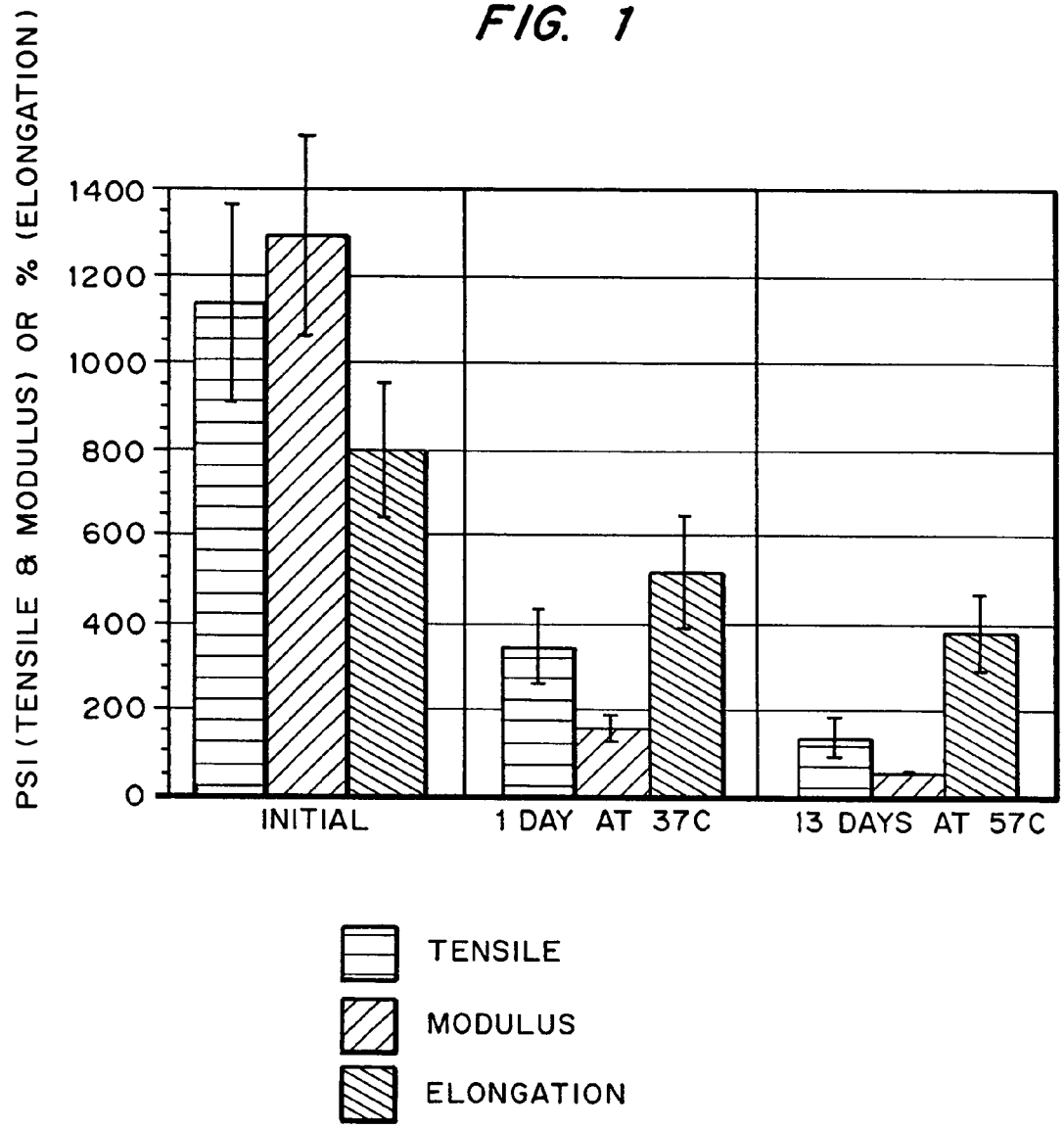
FIG. 1 is a graph of the mechanical properties, tensile strength and modulus, psi, and percent elongation. These are shown for the material as initially formed, for the material after hydration (swelling) for 1 day at 37° C., and for the material after accelerated incubation for 13 days at 57° C.

A range of materials can be used to obtain the desired hydrogel. The key attributes of the formed hydrogel are low swelling at high proportions of solids, high tensile modulus, significant elongation to failure, biocompatibility, and adherence, as defined below.

SWELLING and HYDRATION: Swelling results from the absorption of water by a formed polymeric material, which can be initially dry or already contain water. It is expressed herein as the percent increase in weight of a material from its initial state to a state in equilibrium with an aqueous solution, such as water or a bodily fluid. For example, if a piece of material had a weight of 1 g when formed, and 2 g after equilibration with water, it would exhibit a swelling of 100%. Direct measurement of volume could also be used to determine the degree of swelling. An appropriate time and temperature for obtaining near-equilibrium hydration of a material, in configuration relevant to implant application, is incubation for about 24 hrs in water, ideally at 37° C. to simulate body temperature. However, a simple overnight incubation at room temperature normally gives a hydration, or degree of swelling, that is adequately close to true equilibrium. (It should be noted that this may not be true for other materials—for example, conventional hydrophobic thermoplastics, such as polyethylene).

Prior art gels containing similar materials, such as those described in U.S. Pat. No. 5,410,016 to Hubbell, et al., composed largely or entirely of crosslinked hydrophilic macromers, tend to swell several hundred percent. These gels are highly "elastic" (compliant) and correspondingly do not resist stress well. Hydrogels with relatively little swelling can be made, for example, from dilute crosslinked polyacrylamide, such as gels used for electrophoresis. However, these gels are very brittle and weak and are not suited for the purposes described herein. In these cases, the lack of swelling is achieved in part by having a low percentage of gel-forming solids in the composition. Prior art non-gel materials, such as polylactide, do not swell significantly, but have such a high modulus and hardness that they have a low elastic limit and tend to deform irreversibly or fracture under stress.

Gels with a low degree of swelling are preferred. The most preferred gels have an equilibrium swelling of about 150% or less. Preferred gels have a swelling of about 200% or less. Gels with swelling below about 300% are potentially of use. Low degrees of swelling are achieved at high concentrations of gel-forming solids. Suitable ranges of gel-forming solids at the time of gel formation are at least about 30% by weight, preferably over 40%, more preferably over 50%, and yet more preferably over 60%. The preferred embodiments have over 70% solids at the time of formation. Correspondingly, the concentration of solids after equilibrium swelling is also high. The gel-forming materials should comprise at least 20% by weight of the gel after swelling to equilibrium in bodily fluids. Higher values are preferable, such as 30% or more. The preferred embodiments have 40% or higher solids after equilibration with water.

MODULUS: A material's modulus is the ratio of stress (applied force per unit area) over strain (ratio of compressed or stretched length to original length). It is expressed in units of force per unit area, such as Pascals or PSI, and is typically measured quantitatively on a device such as an Instron® mechanical tester. The gels described herein have a modulus that is quite high for a hydrogel. The most preferred values of the tensile or compressive modulus, at small strains and after swelling, are over 1 megaPascal (MPa). Gels with a post-swelling modulus of 500 kiloPascals (kPa) or greater are preferred. Gels with a modulus of 100 kPa, preferably 200 kPa or more, are of use in the invention. Gels with a modulus above about 50 kPa can be used in low-stress situations.

ELONGATION TO FAILURE: For the purposes described herein, elongation to failure is the strain (degree of deformation) at which the material fails (breaks), expressed as a percent of the material's original length. It is also measured on an Instron® tester or similar device. A material with a 100% elongation (strain) at failure is double its original length. Materials with a significant elongation to failure are preferred. Preferred materials have values above about 300%, and suitable materials can have values in the range of about 25% to over 800% if other properties are appropriate. In addition to the elongation to failure value, having a measurable range in which the material is elastic, i.e., returns to its original shape, is important for its durability, particularly under the conditions found in joints and other orthopedic tissues. As used herein the term "elastic" includes "substantially elastic" and "predominantly elastic" and is used to describe materials that have low modulus in tension or compression and high elongation to break. Substantially elastic materials include materials in which up to 25% of the deformation can be irreversible (plastic) deformation. The deformation of preferred materials is substantially elastic.

TOUGHNESS: The values of elongation and modulus can be combined to give a quantitative measurement of toughness, which is the area under the stress-strain curve to the failure point. However, there are several potential complicating factors, such as rate of elongation and shape of the test piece. For the purposes described herein, the area under the curve should only be used as a means of comparison of related samples. "Toughness" is used herein only in a comparative sense unless otherwise specified. A qualitative measure of toughness, for gels of a particular thickness, is obtained by compressing a piece of gel between the jaws of a locking surgical hemostat. A standard compressive load can be achieved by specifying how many "clicks"—detents giving progressively higher compressive force—on the locking mechanism are used. Gels that do not fracture in this test are tougher than those that do fracture.

BIOCOMPATIBILITY: A material is biocompatible if its implantation does not provoke a severe local or systemic inflammatory reaction. This is in distinction to the transient mild inflammatory response that accompanies essentially all implants. Biocompatibility may be determined by histological examination of the implant site at various times after implantation. One sign of poor biocompatibility can be a severe, chronic, unresolved phagocytic response at the site. Another sign of poor biocompatibility can be necrosis or regression of tissue at the site.

ADHERENCE: Adherence of gels to tissue can be optimized by techniques that employ functional primers, as described in U.S. Pat. Nos. 5,800,373 to Melanson et al., 5,844,016, or 5,900,245 to Sawhney et al. for gels formed by polymerization of ethylenically unsaturated precursors. Suitable gel compositions form strong bonds to tissue. These techniques are also applicable to creating strong adherence of the materials to tissue, including tissue to which it is difficult to obtain adherence by conventional methods, for example, cartilage.

A general procedure for applying materials to orthopedic tissue involves brushing or dabbing primer over a larger area than that over which the material is applied. Thereafter, material is brushed or dabbed over the deposited primer. Then bulk material is applied by dripping (if liquid) or spreading (if paste) over yet a smaller area of the treated zone. Then light (at appropriate wavelength, intensity, distance and for an appropriate time) is applied at each zone, or other means of polymerizing the material are used.

Adherence of the hydrogel to tissue may be determined by passing a 20 gauge needle through the base of the hydrogel near the tissue interface, then grasping the needle at both ends, and finally lifting the needle parallel to the tissue while holding down the test object. The needle eventually releases either via adhesive failure of the hydrogel to the tissue, or by cohesive failure of the hydrogel or tissue. The examples below show many primed hydrogels that provided bonds strong enough to cause cohesive failure.

Adherence may be qualitatively rated as follows. "Excellent adherence" means that upon application of force to the needle, cohesive failure of tissue or gel was observed. "Moderate adherence" means that upon application of force to the needle failure was partially cohesive and partially adhesive. "Fair adherence" means that the mode of failure was adhesive failure. "Poor adherence" means that a light force, as compared with the force needed to cause cohesive failure, was needed to cause adhesive failure. Preferred gels have moderate to excellent adherence on this scale.

LUBRICITY is the quality of a surface that confers relatively low frictional forces between that surface and an opposing surface, often via a thin film of liquid material on the surface that wets both surfaces. The fluid can be adsorbed to the surface, or exuded by the surface, or both. Hydrogels tend to be naturally lubricious. In addition, hydrogel surfaces have an innate affinity for water. Natural cartilage has a similar property.

Gel or hydrogel, as used herein, includes the traditional hydrogel, in which polymer and water each form continuous phases. As used herein, these terms may also include materials absorbing at least 5% of an aqueous phase, which is not necessarily continuous. As used herein "functionally hydrophobic monomers" means monomers including reactive groups and hydrophobic groups and having up to one group that is no more hydrophilic than an alkyl ester or a dialkyl amide. Examples of functionally hydrophobic monomers include vinyl caprolactam (VC), methyl acrylate, methyl methacrylate, styrene, N-vinyl pyrrolidone (VP), and N-vinyl imidazole (VI). In contrast, examples of amphiphilic monomers include diacetone acrylamide (DAA), vinyloxyethanol (VOE), 2-acrylamido-2-methylpropane (AMPS), and methyl acryloyl lactate (ALM) and its relatives.

B. Gel-Forming Precursors

The gel-forming materials comprise reactive polymers (macromers), with molecular weights ranging from about 500 Daltons (Da) to about 200,000 Da, measured by any conventional technique. These macromers contain hydrophobic and hydrophilic regions and are combined, in most embodiments, with reactive low molecular weight monomers, having molecular weights below about 1000 Da. The combination is preferably characterized by being sufficiently hydrophobic after polymerization to provide hydrogels with low swelling and relatively high solids content after equilibration with water. For example, the preferred polymeric solids concentration after equilibration of the formed gel with water or bodily fluids will be in the range of from about 15% wt/wt to above 70% wt/wt. This characteristic may involve phase separation or coacervate formation during polymerization, leading to a heterogeneous hydrogel. Some products may be porous.

1. Macromers

A variety of macromers that can be used to form the hydrogel are described in the literature. A preferred family based on a PEG (polyethylene glycol; poly(ethylene oxide)) backbone and acrylate termination is described in U.S. Pat. No. 5,410,016 to Hubbell et al., U.S. Pat. No. 5,573,934 to Hubbell et al., U.S. Pat. No. 5,800,373 to Melanson et al., U.S. Pat. No. 5,844,016 and U.S. Pat. No. 5,900,245 to Swahney et al. and in International Patent Publication Nos. WO 96/29370 by Board of Regents, University of Texas, and WO 98/2243 and WO 99/07417 by Focal. Design, synthesis and use of such molecules are described. These molecules can readily be adapted for use in the system described herein with little experimentation. Other suitable materials, or materials readily modified to be suitable, are described in U.S. Pat. No. 4,938,763 to Dunn, et al., U.S. Pat. Nos. 5,100,992 and 4,826,945 to Cohn et al, U.S. Pat. Nos. 4,741,872 and 5,160,745 to De Luca et al, U.S. Pat. No. 4,511,478 to Nowinski et al., U.S. Pat. No. 5,198,507 to Kohn et al., U.S. Pat. No. 5,219,564 to Zalipsky et al.; WO 98/00170 by Hennink et al; WO 99/03454 by Hubbell et al.; and U.S. Pat. No. 5,854,382 to Loomis et al.

Macromers which polymerize to form hydrogels via condensation or electrophile/nucleophile chemistry are described in numerous publications, including U.S. Pat. Nos. 5,744,545, 5,614,587, and 5,874,500 to Rhee et al; U.S. Pat. No. 5,514,379 to Weissleder and Bogdanov; U.S. Pat. No. 5,173,301 to Itoh and Matsuda; U.S. Pat. No. 5,583,114 to Barrows et al, and U.S. Pat. No. 4,057,535 to Lipatova et al. Other examples include U.S. Pat. No. 4,839,345 to Doi, et al.; U.S. Pat. Nos. 5,252,714, 5,739,208 and 5,672,662 to Harris, et al.; U.S. Pat. Nos. 4,740,534, 4,994.542, and 4,806,614 to Matsuda, et al.; U.S. Pat. No. 4,804,691 to English et al.; and WO 99/14259 by Harris.

Although poly(ethylene glycol) (PEG) is preferred for forming the macromeric backbone because of its biocompatibility and stability, other macromolecules are also useful. These include, as illustrated below, PEG—PPO (copolymers of polyethylene glycol and polypropylene oxide), hydrophilic segmented urethanes, and multivalently-derivatizable surfactants, in each case derivatized to carry reactive groups. A wide variety of other hydrophilic natural and synthetic polymers are suitable for use in backbones for forming macromers to make the hydrogels. These include hydrophilic synthetic polymers, such as polyvinylpyrrolidone, polyvinyl alcohol (including partially deacetylated polyvinylacetate), poly[meth]acrylic acid and poly[meth]acrylamides (where "[meth]" indicates optional methyl substitution of the acrylate group), and mixed water-soluble copolymers such as copolymers of maleic acid and ethylene. Natural, synthetic and semi-synthetic saccharides and polysaccharides include hydroxyalkyl celluloses, dextran, Ficoll™, bacterial fermentation products such as xanthan or gellan, and food-grade materials such as alginates, carrageenans, pectins, agars, glucomannans, galactomannans, hyaluronic acid, heparin, chondroitin sulfate, and other glycosaminoglycans, and starch. Proteins and nucleic acids can be used. Multivalently-substitutable lipids, such as "dimer fatty acid", monoacylglycerol, phosphatidyl inositol, cardiolipin, and derivatives thereof, can also be used as components of a backbone for forming a macromer.

In some cases, systems containing only macromeric components can be used. It is important in this case that at least some of the macromeric components have significant hydrophobic character, to form hydrophobic domains on polymerization. Suitable backbones for such a macromer, to which polymerizable groups can be grafted, include water-soluble or water-dispersible copolymers of ethylene oxide with propylene oxide and/or butylene oxide, and polyurethanes, polyesters and polyamides containing hydrophilic segments.

2. Monomers

Low molecular weight monomers that are useful in the hydrogel materials share several key properties. The first property is that the monomers should react appropriately in the presence of the other components of the system, in particular a macromeric component or water, when either or both are present. To obtain this property, it is preferable, but not required, that the monomers be miscible with other components of the material. One key material is water at room or elevated temperature, up to about 100° C., with which the monomer is preferably soluble or miscible to a significant extent, such as 30% wt/vol., preferably 40% wt/vol., and most preferably 50% wt/vol. or higher. Alternatively, the monomer can dissolve in or be a solvent for a macromer under similar conditions, in the presence or the absence of water. However, compositions formed of partially immiscible macromers and monomers can be suitable if the polymerization reaction gives the required properties for the final polymerized materials.

The second property is that the monomer should impart the characteristic of low swelling in aqueous solution to the hydrogel upon polymerization. One mechanism for providing decreased swelling is a significant decrease in water absorption of a polymer formed predominantly from the monomer by polymerization. At the high concentration of solids in the hydrogels, a distinctly heterogeneous hydrogel may form upon polymerization, or during subsequent swelling in aqueous solutions.

Thirdly, the product formed from the polymerization of the monomer and the macromer must contain water, or must be capable of absorbing water. This can be as little as 2% to 5% by weight at equilibrium, but preferably is at least 10% and more preferably is 20% or more. This water is important for providing lubricity to the polymerized composition. The material does not need to be a hydrogel at the conclusion of polymerization, if it can absorb or adsorb sufficient water to become lubricious when in contact with bodily fluids.

Unsaturated monomers which have been found experimentally to be preferable for this function include diacetone acrylamide ("DAA"; CAS 2873-97-4). The minimum effective concentration for DAA is about 30% as sole monomer, but may be less in blends with other monomers. These include vinylcaprolactam (VC), vinyloxyethanol (VOE), or up to about 10% of 2-acrylamido 2-methyl propanesulfonic acid (AMPS). It is believed that other low molecular weight monomers are suitable when blended with DAA; suitability and limiting concentrations are readily determined by experimentation. The useful range of monomers increases substantially when the macromer has significant hydrophobic segments or domains.

It is believed that the effectiveness of the preferred low molecular weight monomers is due to a balance of hydrophobic and hydrophilic domains or segments, in the composition after polymerization. The hydrophobic domains serve to control and limit water uptake, and reinforce the polymerized composition which functions as a water-swollen matrix. This is why it is important that at least some of the macromer, or a segment of the macromer, is hydrophilic, and remains hydrophilic after the polymerization; and that a segment of the macromer, or of the monomer after polymerization, be hydrophobic.

A representative class of preferred monomers are acryloyllactic acid-methyl esters (ALM). Methyl acryloyl lactate; the acrylic ester of lactic acid methyl ester; $CH_2=CH-C(=O)OCH(CH_3)C(=O)OCH_3$) is prepared as described in Example 30. The ALM monomer can be viewed as being composed of three parts, generally designated "AHK". "A" designates a reactive group, which in ALM is the residue of acrylic acid after esterification to the hydroxy group of lactic acid. "H" designates a hydroxy carboxylic acid, which is lactic acid in ALM. Finally, "K" designates an alkyl group, or another relatively inert group, containing an alcohol group before esterification to the H carboxyl group. In ALM, the K group is the residue of methanol.

It will be appreciated by those of skill in the art that variants of the ALM structure can readily be manufactured, and will allow the tailoring of the properties of the monomer to a particular tissue situation. For example, each of these groups can be replaced with analogous groups of the same class, resulting in variations in the hydrophobicity, crystallinity, and hydrolysis stability of the materials resulting from the polymerization of these monomers. Thus, A can be selected from acrylic acid and methacrylic acid, or from other acids carrying unsaturation. These include crotonic, isocrotonic, tiglic, angelic, and cinnamic acids, and unsaturated diacids including maleic, fumaric, citraconic, mesaconic, itaconic, citric and isocitric acids, as well as monoesters or monoamides of the dicarboxylic acids.

H can be any of a large number of hydroxy carboxylic acids. These are the residues widely used to create degradability in polymers, so that they will degrade to small, metabolizable or excretable units, in a reasonably predictable way in the body. The most commonly used of these are the lower alkyl hydroxy acids, including glycolic acid, lactic acid, 3-hydroxy-propanoic acid, 2-, 3-, or 4-hydroxybutyric acid, the various isomers of hydroxypentanoic acid (including valeric acid), and the hydroxyhexanoic acid isomers, including 2-caproic acid and 6-caproic acid (epsilon-caproic acid). Many of these hydroxy acids are available in "lactide" or lactone forms, which can simplify synthesis. Other commonly used hydroxy acids include the lactone and hydrolyzed forms of dioxanone (1,4-dioxan-2-one) and other cyclic dioxanones, and of similar 1-oxan-2-one ethers with 5 and 7 membered rings.

In general, when H is formed from the 2-hydroxy acids, the monomers and the corresponding polymers and copolymers tend to degrade by hydrolysis most rapidly, followed by the 3-, 4-, 5- and 6-hydroxyacids. This is due mainly to the hydrophobicity of the higher hydroxy acids. Hydrophobicity tends to exclude water from the labile ester bond between the H and the K group, which slows degradation. Hydrophobicity can also be affected by increasing the hydrocarbon content of the hydroxy acid by incorporation of side chains, such as the methyl group in lactic acid. Likewise, increased hydrophobicity of the K group also slows hydrolysis. Steric protection of the ester linkage from water would also slow hydrolysis. Degradation time is also affected by the crystallinity of the polymer or copolymer. Increases in crystallinity tend to exclude water from the labile ester bond between the H and the K group, which slows degradation. Crystallinity of the polymer or copolymer can be affected by typical factors such as tacticity, molecular weight, etc.

In an alternative structure, H can be the residue of an amino acid, especially of an alpha-amino acid. The linkage between the A and the H group is then an amide linkage. This increases the difference in hydrolysis rates between the A—H linkage and the H—K linkage when K is being removed. For example, glycine ethyl ester hydrochloride is commercially available, and could be acrylated under essentially the same conditions as methyl glycolate (above), particularly after conversion to the free amine. It is expected that it would preferentially de-esterify to form the derivatized lactic acid under the same conditions as ALM (see Example 33). K is an esterified group, which is methyl in ALM. The lower alcohols are preferred as sources of K groups, as they will become innocuous alcohols upon hydrolysis of the ester bond to the H group's carboxyl. These include methanol, ethanol, propanol, isopropanol, isomers of butanol, isomers of pentanol, and isomers of hexanol. More generally, larger alkyls are also suitable, such as those formed from fatty acids (containing up to about 30 carbon atoms), or from sterols (e.g., cholesterol, cholestanol) or other lipid materials with hydroxy groups (e.g., sphingosine). As is known, increase in the size of the K component will tend to increase the hydrophobicity of the material, which will change both its mechanical properties and its degradation time.

Other K groups containing alcohol groups (to provide a readily hydrolyzable linkage) are possible. These may include biologically active molecules, polymers, and other large molecules. Steric considerations will generally require that such monomers be polymerized together with small monomers—for example, AHK molecules with K derived from lower alcohols; or suitable non-AHK polymerizable monomers.

Some of the starting "HK" materials for the synthesis in which an activated "A" group (here, acryloyl chloride) is added to a preformed HK group (here, methyl lactate) are commercially available. These include ethyl and/or methyl esters of lactic, glycolic, 2-hydroxybutyric, 2-hydroxycaproic, and 6-hydroxycaproic acid. However, propyl and higher substituents are not readily available. The amine equivalents (e.g., glycine ethyl ester hydrochloride) have similar availability. A synthetic method for making monomers containing any of a wide range of K groups is described in the examples. The principal requirement of the "K" group is that it contain at least one hydroxyl group.

C. Excipients

Compositions can also include ancillary reagents, such as catalysts or initiators of polymerization; excipients, including buffers; stabilizers; and dye. The compositions will be tailored to accommodate the chemistry or chemistries that are used to polymerize and crosslink the materials.

It should be noted that while reinforcing materials such as fibers and particulates can be added to the hydrogel materials to improve their toughness under load and shear, it is preferable if the hydrogel materials spontaneously form segregated microstructure during polymerization or subsequent hydration. Such materials are thereby "self-reinforcing". This unusual property, when it can be obtained while satisfying other requirements, is a preferred but not required feature.

The hydrogel materials may contain other therapeutic, prophylactic or diagnostic materials which interact with or on the tissues to which the material has been applied. These materials include drugs and other therapeutically active materials, such as proteins, small molecule drugs, nucleic acid molecules, sugars and polysaccharides, lipids, natural extracts, glycosaminoglycans and inorganic compounds. As noted above, excipients such as plasticizers, emollients, fillers, lubricants, buffers, and stabilizers, may also be added. Any of these may be admixed into the material before or during polymerization or crosslinking, and optionally may be encased in liposomes, microparticles, or other delivery forms, for local or systemic delivery.

II. Methods for Polymerization

Any reaction chemistry that is compatible with application in an aqueous environment, and that can be conducted safely on living tissue, is potentially suitable to polymerize the gels. A preferred chemistry involves the use of ethylenically-unsaturated materials, including but not limited to vinyl, acrylic, and alkyl groups ("unsaturated group"). At least some of the macromer or the monomer is preferably substituted (, as terminal or side groups,) so as to be at least difunctional to allow crosslinking in addition to linear polymerization. Reactions with ethylenically unsaturated materials commonly are free-radical chain-growth reactions, and typically are initiated with the use of a chemical initiator or a photoinitiator. Free-radical polymerizable linkages are preferred for forming the hydrogels. The preferred monomers, DAA and ALM, react by this mechanism, and it is convenient to use the same method for crosslinking. However, polymerization and/or crosslinking can be provided by other chemistries, such as those noted above. Any crosslinking or polymerization method that can be used in situ in the body is potentially of use.

An alternative chemistry involves step-growth (condensation) polymerization, and similar heterolytic reactions. For example, a leaving group, such as an N-hydroxy succinimide ester, is easily displaced by a nucleophilic group, such as an amine. To create linear polymers, the preponderance of reactive molecules must have a functionality of two. To create a crosslinked gel, the composition must contain reactive molecules with functionality greater than two. Because polymerization of at least one component to form a low-solubility material is thought to be involved in obtaining the preferred gel compositions, there may be several types of reactive materials in the composition.

Systems of polymerization and crosslinking using both types of chemistry are possible. For example, one component, or a fraction of a component, could carry an electrophilic center with a good leaving group as well as an unsaturated group, while another reactive component could carry nucleophilic groups. Then the first component could polymerize by free radicals, while also becoming crosslinked by the second component. Moreover, certain reactive groups are inherently capable of undergoing several types of crosslinking. For example, a maleimide group can undergo Michael-type addition with a nucleophile such as an amine or thiol, but can also polymerize by free radical polymerization of its double bond. It can also react by hydrolysis of its strained ring, for example by reaction with an amine to form an amide.

Hydrogels can be homo-polymers or hetero-polymers (or co-polymers), interpenetrating networks or semi-interpenetrating networks.

The polymerized materials can be covalently or non-covalently crosslinked. Non-covalently crosslinked materials have a molecular weight after polymerization of less than 200 kDa.

III. Medical Applications

The hydrogels described herein are useful in the treatment of what may be termed "orthopedic tissues". The medical specialty of orthopedics is concerned with the preservation, restoration and development of the form and function of the musculoskeletal system, extremities, spine and associated structures by medical, surgical and physical methods." (Stedman's Medical Dictionary, $25^{th}$ ed., Williams & Wilkins, 1996). Orthopedic tissues include bone, cartilage, and related structures, for example, meniscus, bursa, synovial membranes, and other structures of the joints, as well as tendons, ligaments, muscles and the annulus and nucleus of the vertebral disks. Tissues with similar mechanical properties such as teeth, gums, and gingival ligaments can also be treated effectively with the hydrogel materials.

The properties of the hydrogel forming reagents have been tailored to enable the creation of materials that are hydrogels (as herein defined), and that also adhere well to orthopedic tissues. Such strong adherence can be difficult to achieve with polymeric materials in current uses. For example, fasteners and sculpting of undercuts and hollows in bone and cartilage can be required to obtain good attachment of available polymeric implants. The hydrogel materials described herein are characterized by their strong adherence. When polymerized in the presence of the tissue with the use of appropriate priming techniques, the hydrogels can adhere to tissue with sufficient tenacity that either the gel or the tissue will fail before the adhesive bond between the tissue and the implant is broken ("excellent" adherence, as defined above). "Good" adherence is also acceptable in these materials.

Moreover, these materials have the appropriate mechanical strength and other mechanical properties, such as resilience and stiffness, to withstand the forces applied in these anatomical situations. In addition, the same physical properties make the hydrogels suitable for coating of implants applied to the joints and similar structures. Among the therapeutic benefits provided by these hydrogels is the provision of lubricity to a treated surface. The hydrogel coating can simulate the natural lubricity of an orthopedic surface, such as cartilage, thereby allowing favorable joint articulation while preventing damage as the underlying tissue heals.

Another benefit is the ability to remodel a joint surface by shaping the polymerized deposit with a mold to create or re-create a surface profile of a tissue, such as a condyle. For example, a desired profile can be present in a transparent or highly translucent molding member. The tissue surface is primed with reactive materials as described herein, and the cavity of the mold is filled with materials to form the hydrogel. The filled mold is placed, or is subsequently applied to the tissue surface, so that the unpolymerized materials are in contact with the primed surface. Then the material is polymerized by application of light, or by waiting for polymerization of pre-mixed reactive materials (in which latter case, the mold need not be transparent or translucent). After polymerization, the mold is removed, leaving a dense, lubricious, tightly-adhering hydrogel-forming material having the appropriate profile. Alternatively, if the material is applied as a paste, or physically gels on contact with tissue (for example, because of a temperature change), then it can be shaped to a profile using a scalpel or other instrument before or after polymerization.

Likewise, the hydrogel materials and techniques described herein can be used to resurface damaged sites. For example, the site from which cartilage grafts is taken can be irregular, and be susceptible to damage, or can damage opposing surfaces. Coating or filling the void with the hydrogel materials will prevent ancillary damage while the tissue heals. The material may optionally be designed to be removed by spontaneous degradation, or by controlled abrasion, during this process. A particular advantage of the hydrogel materials, in this and other uses, is that the improved materials can be applied by minimally invasive techniques, for example through a needle or narrow cannula, and polymerized in situ. This makes resurfacing and other operations simpler, and thus less traumatic and less costly, while improving the chances of success. Because the application procedure is simple and minimally invasive, it can be repeated as required to maintain the usefulness of a tissue—for example, a knee joint—and thereby postpone the requirement for a joint replacement or other invasive repair procedure. In such procedures, it is acceptable for the hydrogel-forming implant or surface coating to gradually abrade, as long as the resulting particles are of a size which is appropriate to cause no excessive tissue response. The material can concurrently degrade by simple or enzymatically-catalyzed hydrolysis.

In another use, a torn area of a meniscus can be initially repaired by standard methods, which use pinning and suturing to re-appose the torn segments. A layer of the hydrogel is then applied. The firmly-adherent gel material re-distributes the applied load on the meniscus during healing. Similar uses can be found in other locations in the body, such as in the spine, and in non-limb joints, such as the jaw.

While the hydrogel materials have been described in terms of coatings on tissue or on implants, it is also possible to use these materials as extremely strong yet biocompatible medical adhesives, by coating both surfaces to be adhered with a primer and polymerizing the materials while the materials are in contact with both primed surfaces. Allowance should be made for the predictable expansion of the adhesive during its hydration to equilibrium.

IV. Examples

The present invention will be further understood by reference to the following non-limiting examples.

The examples demonstrate that it is possible to make extremely strong, resilient, low-swelling hydrogels which are biocompatible and which adhere well to orthopedic tissue. The examples also show that the more successful formulations, in terms of having the desired end properties as polymerized gels, have an initial water content before polymerization ranging from 0% up to about 40% (wt/wt). The range giving the best gels was broad: successful formulations were found at 0% and at 33%, and at several concentrations in between.

The remainder of the formulations contained polymerizable materials. Macromers having molecular weights above 500 Da (typically over 1000 Da, and as high as about 100 kDa,) constituted from 0% to about 50% of the weight. The range of about 10% to about 20% was most often successful.

The macromers used were also crosslinking agents. It is believed that the macromers serve two functions, as the crosslinker and as the hydrophilic region, and that these functions could be placed in separate molecules if required. However, the combination of the two functions in one molecule is convenient.

Monomers, with molecular weights below 1000 Da, and more typically below about 500 Da, constituted from about 45% up to 100% of the formulation, typically in the range of about 50% to 90%, and most frequently in the range of about 60 to 80%. The most successful monomers, DAA and ALM, each have hydrophobic groups and more than one hydrophilic group. ALM has two ester bonds, while DAA has an amide and a ketone. The poorly water-soluble ALM could form gels at 100% concentration, which absorbed over 2% of water, and formed better gels when containing a hydrophilic crosslinker. In contrast, the water-soluble DAA, VC or combinations of the two, without a crosslinker, were not suitable as the sole polymerizable component.

In general, polyacrylamide and polyacrylic acid are not suitable as major components of the gel since they are known to swell and form weak gels. It is significant that DAA is amphiphilic, having both hydrophilic and hydrophobic regions, and it is believed that a substantial proportion of the materials in the hydrogel should be amphiphilic. On the other hand, very hydrophobic monomers, such as methyl methacrylate or styrene, form rigid, non-swelling polymers. It is clear from the examples concerning pure ALM that using ALM as the sole monomer produces materials near the low end of the range for water absorption. However, addition of more hydrophilic monomers, particularly crosslinking macromers, imparts an improved degree of hydration as well as improved resiliance. Because the degree of hydrophobicity that is useful is limited, those "AHK" analogs of ALM that have relatively small hydroxy or amino acids, and relatively small ester groups, are preferred. In summary, a preferred composition includes at least about 5%, preferably about 10%, and most preferably about 20% to at least about 50%, of a monomer or macromer having substantial water solubility. Alternatively, the hydrophilicity can be provided by an amphiphilic macromer, even one of low solubility (e.g., certain poloxamers, such as Pluronic-type polymers) having a substantially water-soluble block comprising at least about 20% of the weight of the polymer.

The compositions that are most suitable for these applications form gels that have a maximum equilibrium swelling in water of about 300%, and preferably less than 200%. Values of about 100%, or less, are more preferred. To maintain adequate toughness and tensile properties, the percent of solids in the swollen state should be at least about 20%, preferably 30%, and most preferably 40% or more. To obtain favorable combinations of these properties, a pre-swelling solids content of 40% or more of polymerizable materials is preferred, but this value is secondary to obtaining the required post-swelling values.

The gels both before and after swelling must be resilient, for durability under dynamic conditions of use. A value of the percent elongation to failure of 100% or more is preferred, but smaller elongations, such as 25% to 50%, can be suitable, especially at high solids contents. There is no upper limit on the desirable elastic (reversible) elongation at failure. Some irreversible deformation may also occur. Tensile strength and modulus are clearly important. It is straightforward to obtain a measurement of tensile values, but not as easy to prescribe a limiting value, in part because of the non-criticality of the exact form of the stress-strain curve, in this application. In general, the preferred materials have tensile values of well over 1 MPa before hydration, and of over 0.4 MPa after hydration. Post-hydration values can clearly be lower, especially when the implant or coating is subject to compressive loading with little shear. Post-hydration values of 100–200 kPa are suitable. In some uses, tensile strengths of 20 to 50 kPA can be used.

Example 1

Preparation of PEG-TMC-Diacrylate/DAA Hydrogel

A macromer consisting of a 35 kiloDalton (kDa) core (manufacturer-specified molecular weight; MW about 27 kDa by GPC) of polyethylene glycol (PEG) is reacted with trimethylene carbonate, giving hydroxy-terminated molecules with an average of about two PEG segments and about 15 TMC groups per molecule. This molecule is then end-capped with acryloyl chloride to make it crosslinkable. The molecule is called 35KTA2. Details of synthesis are described in WO 98/12243 by Focal.

A solution was prepared in water which contained by weight about 68% DAA, 15% 35KTA2, about 17% water, and materials for redox-assisted photopolymerization, including Irgacure® 651 (2,2-dimethoxy 2-phenyl acetophenone; DMAP), t-butyl hydroperoxide, and triethylamine as electron carrier and buffer. This was accomplished by adding 3.0 g of 35kTA2 and 13.6 g of DAA to 3.4 g of water, and heating to 70° C. with stirring to complete dissolution. Then 83 microliters of 6% t-butylhydroperoxide (in water) and 30 microliters of molten DMAP were added, with stirring and heating as required for dissolution. The mixture was treated by centrifugation or standing to remove bubbles. It was either stored at minus 40° C. (dark), or used warm (45–50° C.) or at room temperature to form a hydrogel.

This gel-forming material was polymerized by illumination with near-UV light, 350–400 nm band from a xenon source, for about 40 seconds at about 50 to 100 mW per square centimeter, to form bulk gels for testing of mechanical and other properties. When applied to tissue to test adherence, the tissue was primed with a solution prepared as follows. Ferrous gluconate (0.71 g) and 1.42 g D-fructose were dissolved in 100 mL of water. In 7.0 g of this solution, 3.0 g of a low-molecular weight macromer, 3.3 KLA2 (made from nominal 3.3 kDa PEG with an average of five lactate residues per PEG, acrylate end-capped) was dissolved. The primer was applied to the tissue surface with a brush. Priming technology is described in more detail in U.S. Pat. Nos. 5,800,373 and 5,844,016 to Hubbell, et al.; synthesis of the 35KTA2 macromers is described in WO 98/12243 by Focal; and synthesis of the 3.3KLA2 macromer is described in U.S. Pat. No. 5,410,016 to Hubbell et al., along with techniques for photopolymerization.

The bulk properties of the "68 DAA/15 35KTA2" gels are presented in FIG. 1 as formed, after incubation in water for 1 day at 37° C., and after 7 days at 57° C. (accelerated aging).

In Table 1, the preferred material is compared to cartilage and meniscus in mechanical properties: tensile modulus, tensile strength and elongation.

TABLE 1

Material Properties of Bovine Cartilage and Meniscus and Hydrogel

| | Tensile Modulus (MPa) | Tensile Strength (MPa) | Elongation (%) |
|---|---|---|---|
| Articular Cartilage | 3–10 | — | — |
| Meniscus | 50–70 | 5–30 | 15–20 |
| 68 DAA/15 35KTA$_2$/ 17 H$_2$O | 8.9 (as formed) | 8 | 800 |
| | 1.1 (swollen~ 90%) | 2 | 500 |

"Elongation (%)" is length at failure less original length, divided by original length. Tensile strength is secant modulus at maximum stress before failure. The final percent solids was about 40%. The gels scored "Excellent" on tissue adhesion, and passed the clamp (hemostat) test. The gels were turbid (white, nearly opaque) before swelling, and were opaque after swelling. Microscopic examination suggested the presence of heterogeneity in the structure, and possibly the presence of porosity.

Examples 2–27

Synthesis and Comparison of DAA and Other Vinyl-Based Hydrogel Materials

Additional samples of potentially suitable materials were prepared and subjected to a limited set of tests. These samples are shown in Table 2.

TABLE 2

DAA and Other Vinyl-Based Hydrogels

| Example No. | Vinyl Monomers[2] (%)[1] | Macromer(s) (%)[1] | %[1] H$_2$O | Physical Characteristics As Formed[4] | Physical Characteristics After Hydration | % H$_2$O Uptake | % Solids at Equil. | Clamp[5] test | Adherence[6], Notes |
|---|---|---|---|---|---|---|---|---|---|
| 2 | DAA (4.4) | 35KTA$_2$ (20.0) 20KTA$_2$ (5.0) | 60.6 | Soft, elastic | Very soft, elastic | 362 | 6.36 | Pass (swollen) | Cohesive Failure Artic. Cartil. |
| 3 | DAA (60.0) | None | 40.0 | Rigid, opaque, plastic (yielded) | Rigid, opaque, plastic | ~0 | ~60.0 | — | — |
| 4 | DAA (49.1) | 35KTA$_2$ (18.2) | 32.7 | Tough, opaque, resilient | Flexible, opaque, resilient | 139 | 28.1 | | Cohes. Fail. Patella |
| 5 | DAA (54.0) | 3.3KL5 (10.0) | 36.0 | Strong, brittle | Brittle | 93 | 33.2 | | |
| 6 | DAA (41.0) VOE (21.6) | 35KTA$_2$ (10.0) | 27.2 | — | — | 176 | 26.3 | — | — |
| 7 | DAA (51.0) | 35KTA$_2$ (15.0) | 34.0 | Tough, notch resistant | Tough, opaque, flexible | 135 | — | — | — |
| 8 | DAA (68.0) | 35KTA$_2$ (15.0) | 17.0 | Stiff, opaque, notch resistant | Somewhat tough, opaque, flexible | 101 | — | — | — |
| 9 | DAA (49) | 35KTA$_2$ (18) | 33 | Very tough, opaque | — | — | — | — | Cohesive Failure Vertebral disk annulus |
| 10 | DAA (30) | HDI[7]-BDO[7], 3.3KA$_2$ (30) | 40 | Tough, opaque, good tear resistance | Softened after swell | 149 | 24 | Pass 2 click Fail 3 click | — |
| 11 | DAA (60) | HDI[7]-BDO[7], 3.3KA$_2$ (20) | 20 | Stiff, tough, | Stiffer than Ex. 10 | 90 | 42 | — | promising polyurethane macromer |
| 12 | DAA (60) AMPS (2) | Tween A$_3$7 (5) | 20 | — | — | 184 | 31 | — | — |
| 13 | DAA (68) | 35KTA$_2$ (15) | 17 | Tough, opaque | | 87 | 44 | — | Soln. and Paste formulation soln. Cohes. Fail. Paste mixed cohes/adhes Fail to cart, lig., bone |
| 14 | DAA (68) | 35KTA$_2$ (15) | 17 | — | — | — | — | — | Disk annulus, knee cartilage of pig, Cohes. Fail. |
| 15 | DAA (68) | 35KTA$_2$ (15) | 17 | Tough, opaque | — | — | — | — | 7 day sub Q implants - Gel formed in situ-benign tissue response |
| 16 | NIPAM (68) | 35KTA$_2$ (15) | 19.4 | Tough, opaque | Low Mod., Clear | 1018 | 6.6 | Pass | Extreme range of toughness. Loss on hydration |
| 17 | VC (69) | 35KTA$_2$ (26) | 15 | Clear, soft, elastic | Slightly hazy, weakened | 669 | 11.0 | Fail | Low exotherm |
| 18 | VC (26) DAA (43) | 35KTA$_2$ (13) | (18) | Very tough, opaque | Softened | 184 | 28.9 | | — |
| 19 | VI (84) | 35KTA$_2$ (16) | 0 | Did not solidify | — | — | — | — | No water; melted at 82 deg. and cured |
| 20 | MVA (84) | 35KTA$_2$ (16) | 0 | Soft, elastic, clear | Softened clear | 325 | 19.8 | — | — same as last |
| 21 | DAA (59) VC (30) | 35KTA$_2$ (11) | 0 | Rigid, translucent | Soft, opaque | 145 | 40.8 | | Same; Cured as liquid or paste to tough product |
| 22 | DAA (70) | F-88A$_2$ (13) | 17 | Very rigid, translucent | Softened | 51 | 54.8 | | |
| 23 | DAA (70) | F-127 A$_2$ (13) | 17 | Clear, hard, tough | Softened, translucent | 47 | 56.2 | Pass | |
| 24 | VC (33) | F-127 A$_2$ (67) | 0 | Rubbery, clear, tough | Softened, brittle | 219 | 31.3 | Fail | Melted to mix |
| 25 | DAA (50) | F-127 A$_2$ (50) | 0 | Clear, tough | Softened, clear, tough | 155 | 39.2 | Equivocal Pass | Melted to mix |
| 26 | DAA (44) | F-127 A$_2$ (44) | 12 | Clear, tough | Softened, clear, tough | 131 | 38.3 | Pass | Tore cleanly from defect |

TABLE 2-continued

DAA and Other Vinyl-Based Hydrogels

| Example No. | Vinyl Monomers[2] (%)[1] | Macromer(s) (%)[1] | %[1] H$_2$O | Physical Characteristics As Formed[4] | Physical Characteristics After Hydration | % H$_2$O Uptake | % Solids at Equil. | Clamp[5] test | Adherence[6], Notes |
|---|---|---|---|---|---|---|---|---|---|
| 27 | VC (100) | — | — | Yellow, tacky, rigid | Soft, weak, tacky | — | — | — | Very slow cure, inhibited |

Notes to Table 2:
[1]Percent of total formulation
[2]DAA = Diacetone acrylamide; VC = Vinyl caprolactam; VOE = Vinyloxyethanol; MVA = Methyl vinyl acrylamide; AMPS = 2, Acrylamido-2-methyl-propane sulfonic acid; VP = N-vinyl pyrrolidone
[3]t-BHP, t-Butyl Hydroperoxide (250 ppm) for redox with primer
[4]UV cured (40 sec, ca. 100 mW/cm$^2$; 350–400 nm), Irgacure ® 651 Photoinitiator, sometimes added as solution in where the weight of VC is twice the weight of Irgacure ®
[5]Hemostat (2 clicks) applied to specimen, cast and cured as "disk" on Petri dish (see details elsewhere) - swollen unless indicated. Pass means resisted breakthough for more than 5 sec. (preferably for at least 30 sec).
[6]Using 30% 3.3 KL5A2, 500 ppm ferrous gluconate; 1% fructose in water as primer. Adherence test involves inserting 20 gauge needle at base of gel and pulling up parallel to base. The ratings "E", "M", "F", and "P" correspond with "excellent adherence", "moderate adherence", "fair adherence", and "poor adherence", respectively.
[7]BDO = 1.4-Butanediol; HDI = Hexamethylene diisocyanate; F-127 = Pluronic "F-127 copolymer; Tween A3 = Tween" surfactant, triacrylate; P-65 = Pluronic P-65 copolymer
[8]NIPAM = N-Isopropylacrylamide; VC = N-vinyl caprolactam; DAA = Diacetone acrylamide, VI = N-vinyl imidazole
[9]"Plu" = Pluronic F-88 or Pluronic F-127 copolymer Examples 2–27 demonstrate certain formulations that polymerize to produce hydrogels acceptable for orthopedic applications, as well as selected control materials.

Example 2 shows a "classic" hydrogel which, although it contains some (4.4%) DAA, and although it adheres well to tissue, has a high swelling and low final solids concentration. It is too soft for use in a load-bearing application, because its final polymer concentration (6.36% solids) is too low.

Example 3 shows that DAA without a crosslinker forms a plastic with a yield point, rather than a highly resilient material.

Examples 4, 5, 7, and 9 show variations of the preferred formula, which is depicted in example 8. Like example 8, these examples also yield hydrogel materials useful for orthopedic applications.

Example 6 shows partial substitution of DAA with a charged monomer.

Examples 10 and 11 show the use of a polyether urethane backbone, the synthesis of which is described below in Example 28.

Example 12 shows use of a surfactant, polyoxyethylene sorbitan monolaurate (Tween® 20), which has been derivatized to contain about three acrylic groups per molecule, as a hydrophilic crosslinking macromer.

Examples 13 and 14 show adherence of the preferred formula of Examples 1 or 8 to various tissues. Example 13 also compares the preferred formulation as a solution (after heating) versus as a paste, as obtained without heating, or on thawing from the frozen state without heating. The paste is less adherent, giving "Moderate" rather than "Excellent" adhesion.

Example 15 summarizes a subcutaneous implantation experiment (in rats) with the preferred formulation. Good biocompatibility (minimal tissue response) was found.

Examples 16 and 17 show that complete substitution of N-isopropyl acrylamide (NIPAM) and vinylcaprolactam (VC) for DAA gives gels that swell extensively and thereby lose toughness. However, Example 18 shows that VC can partially substitute for DAA with retention of desirable properties. Since DAA is more hydrophobic than VC, this effect may demonstrate desirability for hydrophobicity in the material.

Examples 19–21 show non-water-containing formulations, made by co-dissolving the macromers and the monomers with heating. Example 19 is unsuitable; Example 20 is marginal but acceptable; and Example 21 is essentially the same as Example 18, which contained water during polymerization. Note that Example 20 uses methyl vinylacrylamide (MVA) as monomer, and does not contain DAA.

Examples 22–26 show various formulations in which the macromer is an acrylated poloxamer (i.e., PEG—PPO block copolymer), made by simple acrylation of commercial materials, such as the Pluronic® surfactants by BASF. These macromers, which have hydrophobic segments, can also form hydrogel materials for orthopedic use. However, the formulation with VC is relatively brittle, while the DAA-containing formulae are acceptable.

Example 27 shows that VC alone is not satisfactory, as expected from the absence of crosslinking.

Example 28

Hydrogels Based on Polyurethane-Based Macromers

The reaction of PEG or poloxamer diols and, optionally short-chain diols with diisocyanates, produces macromeric diols which can be reacted with acryloyl chloride, optionally after reaction to provide degradable linkages, to provide acrylic-functional macromonomers with a wide range of properties from soft and weak to quite tough. These versatile compositions allow control of solubility and hydrophobicity.

A macromer with a polyurethane backbone, used in Examples 10 and 11 above, was prepared by reacting 1,4-butanediol (1.27 g, 0.0147 m), PET, MW 3,400 (50.00 g, 0.0147 m) and 1,6-diisocyanatohexane (4.66 g, 0.0277 m) in toluene with dibutyltin dilaurate catalyst (80° C., 4 hr.). The resulting macrodiol was acrylated with acryloyl chloride and isolated by precipitation with hexane. This material was used in an adhesive/sealant formulation, shown in Example 10, by mixing it (3.0 g) into a solution of DAA (3.0 g) in water (4.0 g). This solution was warmed and 6% aqueous t-butyl hydroperoxide (42 mL) along with molten Irgacure® 651 (15 µL) were mixed in. The resulting formulation was treated to remove bubbles by centrifugation or allowing it to stand at ambient and stored at −40° or used to prepare hydrogel.

A similar preparation was used in Example 11 by mixing 2 g of the acrylated polyurethane with a solution containing 6 g of DAA and 2 g of water; the other ingredients were the same.

Example 29

In Vivo Testing of Orthopedic Hydrogel

An acute implant study was performed with the preferred composition DAA (68%)/35KTA2 (15%)/$H_2O$ (17%), on a rabbit medial femoral condyle in which a 3 mm×1 mm defect had been created. A strong bond was formed between the hydrogel implant and the cartilage and bone to which it had been applied.

A 10 day study showed that the hydrogel remained in place with no apparent damage. Surrounding tissue was found to be comparable to untreated, injured controls, demonstrating short-term biocompatibility. In particular, histological sections showed no apparent damage or injury to adjacent cartilage, either in the chondrocytes or in the matrix. The materials used in this study had previously passed cytocompatibility tests and were sterile and non-pyrogenic. The results indicated that the hydrogel replaced cartilage tissue, caused no damage, and allowed function of the joint for the duration of the study.

Example 30

Synthesis, Polymerization, and Testing of PolyALM

Acryloyllactic acid-methyl ester was designed for the formation of orthopedic materials. Acryloyllactic acid-methyl ester (ALM; methyl acryloyl lactate; the acrylic ester of lactic acid methyl ester; $CH_2=CH-C(=O)OCH(CH_3)C(=O)OCH_3$) was prepared as follows.

A 15.61 g amount of methyl lactate (isomer S(-)) in 81 mL toluene was reacted with 13.79 g acryloyl chloride in the presence of 15.79 g triethylamine at less than 20° C. The acryloyl chloride was added drop-wise with cooling to the reaction mixture containing the TEA, to control the exotherm. The resultant TEA.HCl salt was filtered off; and the ALM/toluene solution was purified by passing it through a column containing 15 g alumina, and stabilized with 6.5 mg hydroquinone. The ALM product was isolated by removal of toluene under vacuum using a rotary evaporator.

The ALM yield ranged from 72% to 75%. Based on analysis by Proton-Nuclear Magnetic Resonance Spectroscopy (H-NMR), the amber product typically contains: 94.4% ALM, 1.0% acryloyllactic acid ethyl ester (ALE), 0.0% TEA.HCl, 1.43% methyl lactate, 0.72% acrylic acid, and 1.45% toluene.

Then the ALM was distilled under vacuum at 60–62 C. and 0.8–0.95 mTorr, yielding a clear, colorless fluid. Based on analysis by H-NMR, the ALM typically contains: 98.01% ALM, 0.74% ALE, 0.0% TEA.HCl, 1.43% methyl lactate, 0.22% acrylic acid, and 0.02% toluene.

Polymer A: A neat solution of 150 g ALM was auto-polymerized under vacuum at 60–70° C. for about 20 minutes (exotherm to 120° C.). The very elastic, ultra high molecular weight (MW) polymer required breaking of the reaction vessel for removal. The polymer swelled and or showed partial solubility in most organic solvents, including chloroform, methylene chloride, dimethyl sulfoxide, tetrahydrofuran, hexafluorisopropanol, but was not soluble in water. This material hydrated 2.7% over a period of 3 days at 37° C. and had a modulus of 338.64 kPa after vacuum drying.

Polymer B: A neat solution of 1.95 g ALM was polymerized under $N_2$ with 10.0 mg benzoyl peroxide as initiator by heating at 60–70° C. for about 5 minutes. The elastic, high MW polymer required breaking of the reaction vessel for removal. This polymer had a modulus of 29.55 kPa.

Polymer C: A low MW equivalent was prepared by polymerization of 2.45 g ALM with 30.2 mg benzoyl peroxide as initiator by heating at 60–70° C. for about 5 minutes. This polymer had a modulus of 16.2 kPa. Both Polymers B and C were very flexible and soluble in most organic solvents, including chloroform, methylene chloride, dimethyl sulfoxide, tetrahydrofuran, but were not soluble in water.

A 0.2261 g piece of the high MW polyALM (Polymer B) was incubated with about 30 mL of phosphate buffer pH 7.4 at 37° C. The sample weight was 0.2272 g after 3 days. The material was dried for 24 hrs under vacuum at room temperature. The weight decreased to 0.2212 g, indicating an equilibrium hydration of about 2.2%. This demonstrates that although the high MW polyALM was insoluble in water, it absorbed water to at least 2.2% by weight. The hydrated polyALM was lubricious rather than tacky. The modulus of this incubated polymer was 44.18 kPa.

A 0.3163 g amount of the low MW polyALM (Polymer C) was incubated with about 30 mL of phosphate buffer pH 7.4 at 370° C. The sample weight was 0.3131 g after 3 days. The material was dried for 4 hrs under vacuum at room temperature. The weight decreased to 0.2967 g, indicating an equilibrium hydration of about 5.2%. This demonstrates that although the low MW polyALM was insoluble in water, it absorbed water to at least 5.2% by weight. The hydrated polyALM was lubricious rather than tacky. The modulus of this polymer was 26.95 kPa.

Polymers A, B, and C were incubated at 85° C. in water at pH 11.8–12.5. After 8 days, Polymer A had substantially dissolved. The aqueous solution was viscous. Polymers B and C substantially dissolved over 6 days at 85° C. The aqueous solutions were somewhat viscous.

Mechanical properties of the swollen (24 hrs) and unswollen poly ALM, Polymers A, B, and C, include:

a) all three materials passed the forceps test for toughness; and
b) all three materials had an extension to break of at least 100%.

A sensory test (manipulation) indicated that the materials were both deformable, but would probably be sufficiently tough to protect cartilage.

Thus, polymers of ALM can be prepared to have moduli, toughness and hydration appropriate for application to orthopedic tissues, and further are degradable in an accelerated test.

Example 31

ALM-Containing Copolymers

ALM was copolymerized with other materials. Combinations tested included:

a) 17% 35KTA2 macromer (see description in Table 2), 18% water and 65% ALM, mixed in that order by heating to about 70° C. This mixture was polymerized with UV light in the presence of 0.3% Irgacure® photoinitiator. The resulting material was opaque, and felt somewhat porous. After incubation with water, the material was lubricious and had apparently swelled, but it failed the forceps test.

b) 60% ALM, 30% vinyl caprolactam (VC), and 10% 35KTA2 were mixed by heating to about 70° C. This mixture was polymerized with UV light in the presence of 0.3% ppm Irgacure® photoinitiator. The as-polymerized material was clear, but turned opaque on brief incubation with water. The material was rigid and slightly brittle before hydration, but swelled about 40% and became resilient and plastic after overnight hydration. Elongation to break was over 50%, and the material passed the forceps test for toughness. The compressive modulus of the hydrated material was 151 kPa.

c) 75% ALM, 15% VC, and 10% 35KTA2 were mixed by heating to about 70° C. This mixture was polymerized with UV light in the presence of 0.3% ppm Irgacure® photoinitiator. The as-polymerized material was clear, but turned opaque on brief incubation with water. This material was less rigid and less brittle than the material described in example b) before hydration, but this material swelled about 40% and became resilient and plastic after overnight hydration. Elongation to break was over 50%, and the material passed the forceps test for toughness. A folded hydrated disc sprang back to its original shape in less than 5 seconds, whereas an equivalent disc from material described in example b, above, required about 30 seconds to spring back.

d) 90% ALM and 10% 35KTA2 were mixed by heating to about 70 C. This mixture did not polymerize within 5 minutes with UV light in the presence of 0.3% ppm Irgacure® photoinitiator.

Examples 30 and 31 demonstrate that a material useful as an orthopedic repair material, as defined herein, can be made from a degradable material. Based on these examples, one of skill in the art can make a new material, which has the desired properties of low swelling at high proportions of solids, high tensile modulus, significant elongation to failure, biocompatibility, and adherence.

Example 32

AHC Monomers

Step 1. Synthesis of ALA (Acryloyl lactic acid). The ALM material described above is a convenient starting material for this synthesis, because methyl lactate is commercially available. Acryloyl chloride can be substituted with other active ethylenically unsaturated compounds, for example acryl imidazole or methacryl bromide or cinnamoyl succinimide, depending on the active group desired in the AHK material.

ALM is hydrolyzed to ALA by selective de-esterification in basic aqueous solution. The reaction takes advantage of the more rapid hydrolysis of the methyl lactate ester (the H to K bond) compared to the acryloyl-lactyl ester (the A to H bond). In a typical procedure, 10.03 g of ALM (92.92% pure) is dispersed in 90 mL of water and hydrolyzed with 5.45 mL of 10 N sodium hydroxide to the Na-acryloyllactic acid salt. The base is added dropwise at 20–25° C. The Na-acryloyllactic acid salt is converted to acryloyllactic acid (ALA) with 6N HCl at pH 1.0. The ALA is extracted from the aqueous phase with 112 mL toluene overnight using a liquid—liquid extractor. Residual moisture is removed with 6 g of magnesium sulfate. After filtration of the magnesium sulfate, the toluene is removed under vacuum using a rotary evaporator. The concentrated ALA is a yellow colored oil. Typical analysis of ALA by $^1$H-NMR:

| % ALA | % Toluene | % Lactic Acid | % Acrylic Acid |
| --- | --- | --- | --- |
| 95.78 | 2.53 | 0.16 | 1.53 |

It was determined experimentally that the above conditions optimized the yield of acryloyllactic acid (ALA), in that most of the ALM had hydrolyzed but significant hydrolysis of the acryloyl-lactyl ester bond had not begun.

Step 2. Synthesis of ALC (acryloyl lactoyl chloride, $CH_2=CH-CO-OCH-O-CH(CH_3)-CO-Cl$). This step is a straightforward activation reaction for a carboxylic acid, and many procedures are known for such activation.

In a typical procedure, crude ALA (free acid) was taken up in tetrahydrofuran (THF), and an excess of oxaloyl chloride and a catalytic amount of dimethylformamide (DMF) were added. After incubation for about 20 minutes at 0° C., the reaction was essentially complete. The crude reaction mixture was used directly for the next step.

Step 3. Synthesis of AHK esters. This is simply a reaction of an active carboxyl, such as an acyl chloride, with an alcohol. Many such procedures are known in the literature. The following hypothetical experiment illustrates the general method.

Rather than purifying the ALC, it is most convenient and efficient to add this ALC containing solution directly to a desired alcohol in a suitable solvent along with a suitable amine (e.g. pyridine or triethylamine) to scavenge generated acid. For example, the above THF solution containing ALC can be added to a solution of 0.9% equivalent of cholesterol in toluene, based on the calculated ALA content and triethylamine. After completion of the reaction, the cholesterol ester of ALA is obtained after removal of the amine salt and concentration on a rotary evaporator under reduced pressure.

The activation of the free acid (e.g. ALA) to the activated ester (e.g., ALC) and subsequent synthesis of an AHK ester can also be accomplished as a single or stepwise "one-pot" activation, using suitable acylating agents—for example, dicyclohexylcarbodiimide (DCC) with a catalytic amount of dimethylaminopyridine. A variety of groups can be used as leaving groups C. These include a halogen, a residue of a succinimidyl group, a residue of imidazole, a residue of a thioester, nitrophenols, pyridines, and o-acyl ureas. The key requirement is that the leaving group be readily displacable by an nucleophilic reagent, such as a hydroxyl group, an amine, or a thiol.

Example 33

Acryl-Lactate Ester of a Polymer

Polyvinyl alcohol (PVA) was reacted with ALC to form the monomer acryloyl-lactyl-PVA. ALC was prepared essentially as described above. PVA from Aldrich had a stated molecular weight of 10 kDa (however the actual weight was from 9 kDa to 10 kDa) and was stated to be about 80% hydrolyzed. Ten grams of PVA were placed in a 3-neck 250 mL flask and pyridine was added to about 200 mL final volume. The mixture was stirred under nitrogen to dissolve the PVA. The flask was heated to about 95° C. and distillation of pyridine began. The PVA began to precipitate at about 120° C.; addition of about 200 mL of dimethylacetamide (DMAC) produced a homogenous solution and reduced the temperature to about 70° C. After reduction in volume by distillation to about 200 mL, the mixture was allowed to cool to 60° C. and ALC (450 µL; approximately 97% purity and activity) was added.

The mixture was maintained at 60° C. under stirring and nitrogen for 20 minutes. Then it was precipitated by pouring it into 1800 mL of toluene with vigorous stirring. The gelatinous precipitate was vacuum filtered. The precipitate was mixed with 200 mL hexanes, and filtered; this was repeated twice. A fine damp powder was obtained and was vacuum dried at 40° C. overnight.

The resulting yield contained 9.18 g. $^1$H-NMR analysis indicated about 0.77 acrylate-lactate substitution per PVA molecule. Free radical polymerization of this monomer failed to yield a gel, as expected from the low degree of substitution and the likelihood of steric hindrance.

Another experiment, in which DMAC was the solvent and 300 µL of pyridine was added along with 450 µL of ALC for a 60 minute reaction time, produced a polymer at 9.2% yield. At 10% polymer in buffered water, this polymer gave a loose gel when copolymerized with about an equal weight of vinyl caprolactone. The copolymerization was carried out using eosin Y as photoinitiator and triethanolamine as electron transfer reagent under visible light.

This study demonstrates that the monomer can include a polymer as the "K" group, and its properties can be tailored by variable degrees of derivatization.

Modifications and variations of the hydrogels and methods for manufacture and use thereof will be obvious to those skilled in the art. Such modifications and uses thereof will be obvious to those skilled in the art.

What is claimed is:

1. A composition for forming a water-absorbing, high modulus polymeric, hydrogel-forming material comprising at least one macromer and at least one monomer,
   wherein the macromer comprises hydrophobic and hydrophilic regions, has a molecular weight of 1000 to 100,000 Da and has at least two covalently polymerizable groups, and the macromer comprises at least 5% (wt/wt) of the composition,
   wherein the monomer contains at least one ethylenically unsaturated group and has a molecular weight of less than 1,000 Da, and
   wherein the monomer comprises at least 30% (wt/wt) of the composition, and
   wherein the composition forms a gel upon polymerization, and wherein the gel is characterized as having the following properties,
   a) absorbing water to less than 300% of its initial weight, on equilibration with water or body liquids;
   b) having a tensile modulus of at least 500 kPa or greater at equilibrium swelling with an aqueous solution
   b) having a solids content of at least 20% after equilibration in water or bodily liquids,
   c) having an elongation to failure of at least 25% at hydration equilibrium; and
   d) being sufficiently biocompatible to permit the treatment or repair of biological tissue, or used as an implant in a patient.

2. The composition of claim 1, wherein the composition is in the form of a fluid or paste.

3. The composition of claim 1, further comprising water.

4. The composition of claim 1, wherein the macromer is poly(ethyleneglycol-trimethylene carbonate-diacrylate).

5. The composition of claim 1, wherein the monomer is selected from the group consisting of vinyl caprolactam, methyl acrylate, methyl methacrylate, styrene, N-vinyl pyrrolidone, and N-vinyl imidazole, diacetone acrylamide, vinyloxyethanol, 2-acrylamido-2-methylpropane, and methyl acryloyl lactate and mixtures and derivatives thereof.

6. The composition of claim 1, wherein the macromer comprises up to 50% (wt/wt) of the formulation and the monomer comprises at least 45% (wt/wt) of the formulation.

7. The composition of claim 6, further comprising less than 40% (wt/wt) water.

8. The composition of claim 4, wherein the monomer is diacetone acrylamide.

9. The composition of claim 1, wherein the monomer has the formula AHK, wherein:
   A is a residue of an ethylenically unsaturated acid that is linked to H by a bond selected from ester and amide;
   H is the residue of a hydroxy carboxylic acid, a carbonic acid, or an amino acid, which is linked to K by an ester bond; and
   K is the residue of an alcohol containing at least one carbon atom.

10. Then composition of claim 9 wherein
   A is selected from the group consisting of acrylic, methacrylic crotonic, isocrotonic, tiglic, angelic, and cinnamic acids; maleic, fumaric, citraconic, mesaconic, itaconic, citric and isocitric acids, and monoesters and monoamides thereof, and mixtures thereof,
   H is selected from the group consisting of glycolic acid, lactic acid, 3-hydroxy-propanoic acid, a hydroxybutyric acid, a hydroxypentanoic acid, hydroxy trimethylene carbonic acid, hydroxy ethylene carbonic acid, hydroxy propylene carbonic acid, hydrolyzed dioxanone, a hydroxyhexanoic acid, an alpha, beta or gamma amino acid of eight carbons or fewer, and mixtures thereof, and
   K is an alcohol containing from 1 to about 10 carbon atoms and at least one hydroxyl group, or a mixture of such alcohols.

11. The composition of claim 10 wherein A is selected from the group consisting of acrylic acid and methacrylic acid.

12. The composition of claim 1, further comprising at least one polymerization initiator.

13. The composition of claim 12, wherein the initiator is selected from the group consisting of chemical initiators and photoinitiators.

14. The composition of claim 13, wherein the initiator is a component for redox-assisted photopolymerization.

15. The composition of claim 1, wherein the macromer comprises polyethyleneglycol.

* * * * *